United States Patent
Patterson (12)

(10) Patent No.: US 6,303,289 B1
(45) Date of Patent: Oct. 16, 2001

(54) COMPOSITION AND METHODS FOR THE TREATMENT OF CANCER AND VIRAL INFECTIONS

(75) Inventor: David Patterson, Denver, CO (US)

(73) Assignee: Elenor Roosevelt Institute, Denver, CO (US)

( * ) Notice: Subject to any disclaimer, the term of this patent is extended or adjusted under 35 U.S.C. 154(b) by 0 days.

(21) Appl. No.: 09/534,420

(22) Filed: Mar. 23, 2000

Related U.S. Application Data

(60) Provisional application No. 60/125,754, filed on Mar. 23, 1999.

(51) Int. Cl.$^7$ .............................. C12Q 1/00; C12N 5/02
(52) U.S. Cl. ................................................. 435/4; 435/375
(58) Field of Search ........................................ 435/375, 4

(56) References Cited

U.S. PATENT DOCUMENTS 5,840,490   11/1998   Bacchetti et al. .................... 435/6

OTHER PUBLICATIONS

Elion, "The Purine Path to Chemotherapy", Science 244: 41–47, 1989.

Kennedy et al., "Identification of HHV8 in Early Kaposi's Sarcoma: Implications for Kaposi's Pathogenesis", J Clin Path: Mol Pathol 51: 14–20, 1998.

Harrington, et al., "A Mammalian Telomerase–Associated Protein", Science 275: 973–977, 1997.

Vaziri et al., "Reconstitution of Telomerase Activity in Normal Human Cells Leads to Elongation of Telomeres and Extended Replicative Life Span", Curr Biol. 8:279–282, 1998.

Jiang et al. "Telomerase Expression in Human Somatic Cells Does Not Induce Changes Associated with a Transformed Phenotype", Nat. Genet. 21:111–114, 1999.

Morales et al., "Absence of Cancer–Associated Changes in Human Fibroblasts Immortalized with Telomerase", Nat. Genet. 21:115–118, 1999.

Barton et al., "Isolation of a Human cDNA Encoding Amidophosphoribosyltransferase and Functional Complementation of a CHO Ade–A Mutant Deficient in this Activity", Som Cell Mol Genet 17:311–322, 1991.

Brodsky et al., "The Human GARS–AIRS–GART Gene Encodes Two Proteins which are Differentially Expressed During Human Brain Development and Temporally Overexpressed in Cerebellum of Individuals with Down Syndrome", Hum Mol Genet 6:2043–2050, 1997.

Patterson, "Biochemical Genetics of Chinese Hamster Cell Mutants with Deviant Purine Metabolism: Biochemical Analysis of Eight Mutants", Somat Cell Genet 1:91–110, 1975.

Oates et al., "A Mutant of CHO–K1 Cells Deficient in Two Nonsequential Steps of de novo Purine Biosynthesis", Cell 20:797–805, 1980.

Chang et al., "Expression of a Human cDNA Encoding a Protein Containing GAR Synthetase, AIR Synthetase and GAR Transformylase Corrects the Defects in Mutant Chinese Hamster Ovary Lacking These Activities", Som Cell Mol Genet 17:441–420, 1991.

Gnirke et al., "Cloning and in vivo Expression of the Human GART Gene Using Yeast Artificial Chromosomes", EMBO J 10: 1629–1634, 1991.

Henikoff et al., "Multiple Purine Pathway Enzyme Activities are Encoded at a Single Genetic Locus in Drosophila", Proc Natl Acad Sci USA 83: 720–724, 1986.

Patterson et al., "Demonstration, by Somatic Cell Genetics, of Coordinate Regulation of Genes for Two Enzymes of Purine Synthesis Assigned to Human Chromosome 21", Proc Natl Acad Sci USA 78: 4305–4309, 1981.

Patterson et al., "Genetics of Somatic Mammalian Cells: Biochemical Genetics of Chinese Hamster Cell Mutants with Deviant Purine Metabolism", Proc Natl Acad Sci USA 71:2057–2061, 1974.

Clark, "Molecular and Genetic Analyses of Drosophilia Prat, Which Encodes the First Enzyme of de novo Purine Biosynthesis", Genetics 136:547–557, 1994.

Ebbole et al., "Cloning and Characterization of a 12–Gene Cluster from *Bacillus subtilis* Encoding Nine Enzymes for de novo Purine Nucleotide Synthesis", J. Biol. Chem. 262: 8274–8287, 1987.

Altschul et al., "Basic Local Alignment Search Tool", J. Mol. Biol. 215:403–410, 1990.

Nagase et al. "Prediction of the Coding Sequences of Unidentified Human Genes. VII. The Complete Sequences of 100 New cDNA Clones from Brain Which can Code for Large Proteins in vitro", DNA Res 4:141–150, 1997.

Shepherd et al., "Preparation and Screening of an Arrayed Human Genomic Library Generated with the P1 Cloning System", Proc Natl Acad Sci USA 91:2629–2633, 1994.

Kunst et al., "Gain of Function in ALS: Mutations in SOD–1 Cause Novel Protein Interactions", Nat Genet 15:91–94, 1997.

Finley et al., "DNA Cloning 2; Expression Systems: A Practical Approach", Oxford University Press, pp. 169–203, 1995.

Saito et al., "Comparative Gene Mapping of the Human and Mouse TEP1 Genes, Which Encode One Protein Component of Telomerases", Genomics 46:46–50, 1997.

(List continued on next page.)

*Primary Examiner*—Robert A. Schwartzman
*Assistant Examiner*—Katharine F Davis

(57) ABSTRACT

Compounds and methods for the treatment of cancer and viral diseases include the administration of viral proteins having substantial homology to BNRF1, FGARAT and/or PRAT. The proteins of the present invention and the nucleic acids encoding such proteins are useful to treat various cancers and uncontrolled cell growth, as well as viral infections, including AIDS. Assays of the present invention are useful in identifying inhibitors of interactions between telomerase, telomeres and viral proteins, especially those that are similar to proteins participating in purine synthesis.

2 Claims, No Drawings

OTHER PUBLICATIONS

Cong et al., "The Human Telomerase Catalytic Subunit hTERT: Organization of the Gene and Characterization of the Promoter", Hum Mol Genet 8:137–142, 1999.

Feng et al., "The RNA Component of Human Telomerase", Science 269: 1236–1341, 1995.

Schnapp et al., "One–Step Affinity Purification Protocol for Human Telomerase", Nucleic Acids Res 26:3311–3313, 1998.

Gura Tracing Leptin's Partners in Regulating Body Weight, Science 287: 1738–1741, 2000.

Barnes et al., "Purification of, Generation of Monoclonal Antibodies to, and Mapping of Phosphoribosyl N–Formylglycinamide Amidotransferase", Biochemistry, 1994, 33, pp. 1850–1860.

Becker et al., "Hyperuricemia and Gout", The Metabolic and Molecular Bases of Inherited Disease, Seventh Edition, vol. II, Chapter 49, pp. 1655–1677 1995.

Kieff, "Epstein–Barr Virus and Its Replication", Fields Virology, Third Edition, vol. 2, pp. 2343–2396 1996.

Collins, "Structure and Function of Telomerase", Current Opinion in Cell Biology, 1996, pp. 8: 374–380.

Bodnar et al., "Extension of Life–Span by Introduction of Telomerase into Normal Human Cells", Science, vol. 279, Jan., 1998, pp. 349–352.

Elion, "The Purine Path to Chemotherapy", Bioscience Reports, vol. 9, No. 5, 1989, pp. 509–529.

Counter et al., "Stabilization of Short Telomerase and Telomerase Activity Accompany Immortalization of Epstin–Barr Virus–Transformed Human B Lymphocytes", Journal of Virology, vol. 68, No. 5, pp. 3410–3414, 1994.

Klingelhutz, AntiCancer Research 19:4823–4830 1999.*

* cited by examiner

US 6,303,289 B1

COMPOSITION AND METHODS FOR THE TREATMENT OF CANCER AND VIRAL INFECTIONS

RELATED APPLICATION

This application claims priority from U.S. Provisional Patent Application No. 60/125,754 filed on Mar. 23, 1999. The entire disclosure of the provisional application is considered to be part of the disclosure of the accompanying application and is hereby incorporated by reference.

FIELD OF THE INVENTION

The present invention is directed to compounds and methods for the treatment of cancer and viral diseases, and is more particularly directed to the role of telomerase or inhibitors of purine synthesis and telomere structures as they relate to purine nucleotide synthesis and analogs and inhibitors of telomerase for the treatment of cancer and viral infections, including AIDS, and also to the use of inhibitors of interactions between telomerase and telomeres and viral proteins which are similar to those that participate in purine synthesis.

BACKGROUND OF THE INVENTION

Purines are critical biological molecules. They act as the precursors for DNA and RNA synthesis, as major components of cellular energy metabolism, as intracellular second messenger signaling molecules, as extracellular neurotransmitters, and as coenzymes for many critical biochemical reactions. All free-living organisms can synthesize purines. The de novo biosynthetic pathway consists of 10 enzymatic steps resulting in the synthesis of IMP. As might be expected, cancer cells, with their increased requirements for DNA and RNA synthesis, generally have elevated rates of purine synthesis. Therefore, it is not surprising that analogues of purines or molecules that inhibit purine synthesis are common anti-cancer drugs.

Viral infection has long been associated with human cancers. One of the first, and strongest, associations is with Epstein-Barr Virus (EBV), which is an etiologic agent in Burkitt's Lymphoma (BL), Hodgkin's disease, some T-cell lymphomas and nasopharyngeal carcinoma. EBV is a DNA virus that is related to the herpes viruses, and the most recent nomenclature recommendation is that it is renamed human herpes virus 4 (HHV4) (3). Recently, human herpes virus 8 (HHV8) has been strongly implicated as the etiologic agent in Kaposi's sarcoma in AIDS patents. The mechanisms by which EBV viral infection may work are still being clarified. Since viruses put heavy demands on the host DNA and RNA synthesis machinery, it may well be that during viral infection there is an elevated requirement for purine synthesis. Specifically, viruses may alter or assume control of cellular purine metabolism as a part of viral infection. As with cancer, some of the most effective antiviral agents for example, acyclovir, are purine nucleotide analogues. Interestingly, EBV and other viruses appear to possess genes important for nucleotide metabolism including ribonucleotide reductase, dihydrofolate reductase, and thymidine kinase. So far, no reports of viral genes participating directly in purine synthesis have been published.

SUMMARY OF THE INVENTION

The present inventors have observed an unexpected striking homology between an Epstein-Barr Virus (EBV) protein, BNRF1 (Epstein Barr virus: X67777 or gi:59165), and a critical enzyme of purine biosynthesis, phosphoribosylformylglycinamide (FGAR), amido transferase (FGARAT)(Note: human AB002359 or gi:2224662; FGARAT *Drosophila melanogaster* is: U00683 or gi:414422). Another observation is that FGARAT or a related protein, (e.g., BNRF1), interacts with telomerase, the enzyme responsible for maintenance of telomeres, the ends of chromosomes. One aspect of the present invention, therefore, is directed to the regulation of various enzymes, cofactors and inhibitors that are involved in the stabilization of telomeres, and particularly inhibitors of a protein interaction with telomerase. The present inventors are the first to recognize that a protein encoded by various viruses, such as an EBV virus, is capable of carrying out one of the steps of purine biosynthesis, FGARAT. Because FGARAT interacts with telomerase, which acts to stabilize chromosome ends and is necessary for immortal growth of mammalian cells, the present inventors are the first to recognize that purine synthesis is directly linked to the immortalization process, a critical aspect of malignant transformation. This linkage occurs both because of the necessity for purine synthesis and also because of the interaction by particular proteins with telomerase.

Experiments indicate that viral FGARAT-protein BNRF1 has FGARAT enzymatic activity. Further, BNRF1, FGARAT and a second amino transferase in purine synthesis, amido-phosphoribosyltransferase (PRAT) (NM 002703 or gi:4505978), a rate-limiting step of purine synthesis in cells, also display enzymatic activity having an effect on telomerase function. Thus, another aspect of the present invention relates to the interaction of BNRF1, FGARAT and/or PRAT (hereinafter referred to alternatively as BNRF1-like proteins and/or proteins of the present invention) with telomerase, both in vitro and in vivo. By interfering with the interaction between BNRF1-like proteins and telomerase, one of skill in the art can for the first time regulate immortalization of a cell.

A relatively recent and exciting line of cancer research involves the study of telomerase. Chromosomes of cells all have ends called telomeres. It now appears that telomeres, which are composed of specific DNA repeat sequences, tend to shorten as cells divide. When telomeres get too short, cell division may cease. Telomerase repairs telomeres and maintains them at a size sufficient for continued cell division. Telomerase consists of at least 2 components, a reverse transcriptase subunit and an RNA component. In addition, at least one telomerase-associated protein has been reported. One interesting feature of EBV infection is that it can result in immortalization of human B-lymphocytes, possibly through the stabilization of telomeres and telomerase activity. The mechanism by which the virus accomplishes this, however, has hitherto been a mystery. Recently it has been possible to immortalize human fibroblasts by introducing and expressing the reverse transcriptase subunit of telomerase in these cells. These immortalized fibroblasts lack many other features of transformed cells. The present inventors contend that expression of telomerase is necessary but is not sufficient for immortalization and carcinogenicity. Clearly, one of the consequences of immortalization and cell division will be a requirement for purine nucleotide synthesis.

With respect to de novo purine nucleotide synthesis in animals, the present inventors have isolated Chinese hamster ovary (CHO) cell mutants deficient in each of the 10 enzymatic steps leading to IMP, the first completed purine nucleotide, and regionally mapped all 6 of the genes encoding the enzymes carrying out these steps. Using the CHO mutants, the present inventors have cloned the genes for a number of these enzymes in functional form using complementation of CHO mutants with cDNA or genomic DNA fragments. Genetic complementation by somatic cell hybridization was used to define independent genes encoding the enzymes of the pathway and the amidophosphoribosyl transferase (PRAT) gene was cloned. The PRAT gene encodes the first committed step of purine synthesis, is allosterically regulated, and is hypothesized to be an important site of regulation of the pathway. The present inventors have used the CHO mutants, and mutants of *Drosophilia melanogaster*, to define the multifunctional nature of the proteins carrying out the enzymatic steps. Using such mutants, the present inventors developed unique biochemical assays for the intermediates in the pathway and for the activities of the enzymes of the pathway. The mutants serve as a convenient source of large amounts of radio-labeled intermediates to use in enzyme assays.

The fourth step of the purine biosynthetic pathway, FGARAT, catalyzes the glutamine dependent amidation of FGAR to FGAM. It is the only enzyme of purine synthesis for which no mammalian gene or cDNA has been reported in the literature. CHO cell mutants of the AbeB complementation group lack detectable FGARAT activity and protein and have an absolute requirement for purines for growth. In addition, the present inventors have reported the isolation of an additional type of mutant, AdePAB, which is deficient in FGARAT activity and protein but is also deficient in (PRAT) activity. PRAT is similar to FGARAT in that both are amidotransferases. However, there is no significant DNA sequence homology between the PRAT and FGARAT genes. CHO mutants of the AdeA complementation group lack PRAT activity but have FGARAT activity (AdeB mutants have PRAT activity). Based on several genetic observations, AdePAB mutants are believed to be altered in a third gene, not the PRAT or FGARAT genes. First, in humans and *Drosophila melanogaster* the genes for PRAT and FGARAT are on different chromosomes; second, Ade-PAB mutants revert; and third, they can be complemented by other CHO cell mutants or wild-type CHO cells but not by members of the AdeA or AdeB complementation groups. Therefore, AdePAB mutants cannot be deletions, and they must regulate the activities of the PRAT and FGARAT genes or proteins in trans. In some microorganisms, B. subtilis for example, it seems to be essential to maintain equimolar amounts of PRAT and FGARAT, and this is thought to be accomplished through regulation of protein synthesis. The inventor proposes that telomerase may be the regulator of FGARAT and PRAT, thus resulting in direct linkage of purine synthesis, maintenance of telomeres, and the cellular immortalization necessary for cancer.

AdeB CHO cells accumulate very large amounts of the substrate of the enzyme, FGAR. Based on this appreciation, the present inventors have developed a very sensitive and direct assay for FGARAT activity. The present inventors purified FGARAT from CHO cells and produced monoclonal antibodies which recognize the human protein. Using antibodies recognizing human FGARAT and a human/CHO somatic cell hybrid gene mapping panel, the gene was regionally mapped to chromosome 17p. The present inventors have cloned a functional human FGARAT using the *Drosophilia melanogaster* FGARAT cDNA sequence. An anonymous human cDNA was identified with 50% amino acid identity to the Drosophila enzyme. The present inventors obtained this clone and used PCR primers designed from the clone to isolate a human genomic P1 clone. This clone can be transfected into AdeB CHO cells and eliminates their requirement for purines for growth. These transfected clones express human FGARAT protein by Western blot analysis and human mRNA by Northern blot analysis.

Computer analysis of the FGARAT sequence shows that it has extensive homology to the EBV late protein BNRF1. The probability that this result is non-significant is $2.5e^{-58}$. This protein encodes the major virion external non-glycosylated protein and is expressed late in infection. it is believed to be a viral tegument protein. BNRF1 is homologous to tegument proteins from many other herpes viruses, e.g., HHV8, which is thought to be responsible for the Kaposi's sarcoma seen in individuals with AIDS.

The present inventors are the first to appreciate the importance of the observation that FGARAT, or related proteins like BNRF1, (e.g., BNRF1-like proteins) interact with telomerase. There is an elevated level of FGARAT activity (20 to 60-fold) in human cancer tissue as compared with normal human tissue. Moreover, the present inventors are the first to appreciate that BNRF1 has FGARAT activity. One aspect of the present invention is therefore a method for using specific inhibitors of viral proteins to control host cell purine nucleotide synthesis during viral infection. The biological significance to the interaction with telomerase is that such interaction regulates purine synthesis and vice versa. Telomerase is therefore a transregulator that is altered in AdePAB mutant CHO cells.

One aspect of the present invention therefore relates to a method for immortalizing a cell by administering to a mammal an effective amount of a compound comprising a protein having significant homology to a viral protein, including but not limited to BNRF1 and BNRF1-like proteins. In yet another embodiment, such protein further has significant homology to FGARAT and/or PRAT.

Yet another embodiment of the present invention relates to a method to identify a compound that regulates the immortalization of a cell, comprising contacting a cell with a putative regulatory compound, wherein the cell includes a telomere and telomerase; and assessing the ability of the putative regulatory compound to regulate the activity of telomerase. Even more preferably, the method to identify a compound further comprises assessing the ability of the putative regulatory compound to interfere with the interaction between a viral protein, including but not limited to BNRF1, and telomerase.

The above method can be practiced on cells selected from the group consisting of b-lymphocytes, cancer cells, fibroblasts, Langerhans cells, epithelial cells, monocytes and dendritic cells. The putative regulatory compound is preferably selected from the group consisting of a small organic molecule, a peptide and a polypeptide.

A further aspect of the present invention is directed to a regulatory compound identified by the compound's ability to regulate a biological function selected from the group consisting of stabilization of a telomere within a cell, immortalization of a cell, regulation of a cell's malignant growth and regulation of purine biosynthesis within the cell. The regulatory compound is preferably capable of penetrating the plasma membrane of a cell and of inhibiting the ability of a protein, which shares substantial homology with BNRF1, and such protein's interaction with telomerase. Such regulation may involve the step of binding to telomerase so as to preclude binding of the BNRF1-like protein, interference with the ability of the BNRF1-like protein itself to bind and/or interact with telomerase, or to interact with a co-factor involved in the association between the BNRF1-like protein and telomerase.

Yet a further aspect of the present invention is directed to a method to treat an animal with a disease selected from the group consisting of a disease involving malignant cells and a disease involving an autoimmune disease, said method comprising administering to an animal an effective amount of a therapeutic composition comprising a compound that controls the regulation of a protein capable of interfering with the association between a BNRF1-like protein and telomerase. The diseases capable of treatment with the present invention include cancer and uncontrolled cell growth, as well as the aging of cells. Indeed, one aspect of the present invention relates to a method for affecting the immortalization of a cell either by rendering an immortal cell mortal or alternatively, by transforming an mortal cell to become an immortal cell. The ability to regulate the mortality of a cell is accomplished by administering to a cell in an effective amount a protein sharing significant homology with BNRF1 and/or FGARAT, thereby stabilizing telomeres by interacting with telomerase produced by the cell.

In one embodiment of the invention, a yeast interaction test (e.g., Finley and Brent) is utilized to determine whether a viral protein or FGARAT or PRAT of the present invention and telomerase interact. Using such tests, putative compounds can be screened to select appropriate compounds that interfere with the viral (or FGARAT or PRAT) protein and telomerase association. Such putative compounds can then be further explored for use as effective agents in treating cancer. Preferably, inhibitors of the viral protein and telomerase interaction will not also substantially interfere with the interaction between cellular proteins and telomerase.

In another embodiment of the invention, particular small molecule inhibitors of viral BNRF1 and/or FGARAT activity, but not cellular FGARAT activity, will be identified using the enzyme assays, reagents, and cell lines developed by the inventor. Such molecules are potential therapeutic agents and treatments for cancer and viral infections.

It is within the scope of the present invention to use antisense technology to prohibit the production of particular proteins (e.g., BNRF1-like proteins) that associate with telomerase, thereby regulating the stability of telomeres within a cell.

Particularly preferred inhibitors of proteins having FGARAT-like and/or BNRF1-like activity of the present invention are glutamine analogs and diazoxonorleucine (DON).

DETAILED DESCRIPTION OF THE PREFERRED EMBODIMENT

There are various aspects of the present invention which will be described below, including but not limited to the following:

1. The isolation of nucleic acid sequences encoding for proteins/enzymes having the ability to stabilize a telomere, particularly those enzymes that interact with telomerase. Preferably, such proteins/enzymes are different from those expressed in a host, for example are of viral origin and are capable of being regulated without interfering with normal cellular proteins/enzymes that associate with telomerase.

2. Various analogs of the nucleic acid sequences, having effective homology/percent identity as the proteins/enzymes described above and that have substantially the same function;

3. Recombinant/molecules;

4. Recombinant cells;

5. Expression vectors;

6. Assays and kits to test for particular enzymatic activity of particular proteins and/or peptides and/or mimetopes, including those that have FGARAT-like and/or BNRF1 like activity, and further including the ability to interact with various other enzymes involved in the stability of telomeres and/or the regulation of telomerase and/or purine biosynthesis;

7. Methods to determine interactions between telomerase and proteins of the present invention, and in particular, to determine whether such proteins effect the stability of telomeres and/or activity of telomerase in normal cells, cancer cells and cells infected with viral proteins.

According to one embodiment of the present invention, homology or percent identity between two or more nucleic acid or amino acid sequences is performed using methods known in the art for aligning and/or calculating percentage identity. To compare the homology/percent identity between two or more sequences, for example, a module contained within DNASTAR (DNASTAR, Inc., Madison, Wis.) can be used. In particular, to calculate the percent identity between two nucleic acid or amino acid sequences, the Lipman-Pearson method, provided by the MegAlign module within the DNASTAR program, is preferably used, with the following parameters, also referred to herein as the Lipman-Pearson standard default parameters:

(1) Ktuple=2;

(2) Gap penalty=4;

(3) Gap length penalty=12.

According to another embodiment of the present invention, to align two or more nucleic acid or amino acid sequences, for example to generate a consensus sequence or evaluate the similarity at various positions between such sequences, a CLUSTAL alignment program (e.g., CLUSTAL, CLUSTAL V, CLUSTAL W), also available as a module within the DNASTAR program, can be used using the following parameters, also referred to herein as the CLUSTAL standard default parameters:

Multiple Alignment Parameters (i.e., for more than 2 Sequences)

(1) Gap penalty=10;

(2) Gap length penalty=10;

Pairwise Alignment Parameters (i.e., for two Sequences)

(1) Ktuple=1;

(2) Gap penalty=3;

(3) Window=5;

(4) Diagonals saved=5.

As used herein, stringent hybridization conditions refer to standard hybridization conditions under which nucleic acid molecules are used to identify similar nucleic acid molecules. Such standard conditions are disclosed, for example, in Sambrook et al., *Molecular Cloning: A Laboratory Manual,* Cold Spring Harbor Labs Press, 1989. Sambrook et al., ibid., is incorporated by reference herein in its entirety (see specifically, pages 9.31–9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267–284; Meinkoth et al., ibid., is incorporated by reference herein in its entirety.

More particularly, stringent hybridization and washing conditions, as referred to herein, refer to conditions which permit isolation of nucleic acid molecules having at least about 70% nucleic acid sequence identity with the nucleic acid molecule being used to probe in the hybridization reaction, more particularly at least about 75%, and most particularly at least about 80%. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6×SSC (0.9 M Na$^+$) at a temperature of between about 20° C. and about 35° C., more preferably, between about 28° C. and about 40° C., and even more preferably, between about 35° C. and about 45° C. In particular embodiments, stringent hybridization conditions for DNA:RNA hybrids include hybridization at an ionic strength of 6×SSC (0.9 M Na$^+$) at a temperature of between about 30° C. and about 45° C., more preferably, between about 38° C. and about 50° C., and even more preferably, between about 45° C. and about 55° C. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 TO 9.62.

In accordance with the present invention, an isolated nucleic acid molecule is a nucleic acid molecule that has been removed from its natural milieu (i.e., that has been subject to human manipulation). As such, "isolated" does not reflect the extent to which the nucleic acid molecule has been purified. An isolated nucleic acid molecule can include DNA, RNA, or derivatives of either DNA or RNA. There is no limit, other than a practical limit, on the maximal size of a nucleic acid molecule in that the nucleic acid molecule can include a portion of a gene, an entire gene, or multiple genes, or portions thereof.

An isolated nucleic acid molecule of the present invention can be obtained from its natural source either as an entire (i.e., complete) gene or a portion thereof capable of forming a stable hybrid with that gene. An isolated nucleic acid molecule can also be produced using recombinant DNA technology (e.g., polymerase chain reaction (PCR) amplification, cloning) or chemical synthesis. Isolated nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications provide the desired effect. An isolated nucleic acid molecule of the present invention can include degeneracies. As used herein, nucleotide degeneracies refers to the phenomenon that one amino acid can be encoded by different nucleotide codons. Thus, the nucleic acid sequence of a nucleic acid molecule that encodes a protein of the present invention can vary due to degeneracies.

A nucleic acid molecule homologue can be produced using a number of methods known to those skilled in the art (see, for example, Sambrook et al., ibid.). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid and/or by hybridization with a wild-type gene.

Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding an epimerase according to the present invention.

Knowing the nucleic acid sequences of certain nucleic acid molecules of the present invention allows one skilled in the art to, for example, (a) make copies of those nucleic acid molecules and/or (b) obtain nucleic acid molecules including at least a portion of such nucleic acid molecules (e.g., nucleic acid molecules including full-length genes, full-length coding regions, regulatory control sequences, truncated coding regions). Such nucleic acid molecules can be obtained in a variety of ways including traditional cloning techniques using oligonucleotide probes of to screen appropriate libraries or DNA and PCR amplification of appropriate libraries or DNA using oligonucleotide primers. Preferred libraries to screen or from which to amplify nucleic acid molecule include bacterial and yeast genomic DNA libraries, and in particular, microalgal genomic DNA libraries. Techniques to clone and amplify genes are disclosed, for example, in Sambrook et al., ibid.

The present invention includes a recombinant vector, which includes at least one isolated nucleic acid molecule of the present invention, inserted into any vector capable of delivering the nucleic acid molecule into a host microorganism of the present invention. Such a vector can contain nucleic acid sequences that are not naturally found adjacent to the isolated nucleic acid molecules to be inserted into the vector. The vector can be either RNA or DNA and typically is a plasmid. Recombinant vectors can be used in the cloning, sequencing, and/or otherwise manipulating of nucleic acid molecules. One type of recombinant vector, referred to herein as a recombinant molecule and described in more detail below, can be used in the expression of nucleic acid molecules. Preferred recombinant vectors are capable of replicating in a transformed bacterial cells and yeast cells. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, parasite, insect, other animal, and plant cells. Preferred expression vectors of the present invention can direct gene expression in bacterial, yeast, helminth or other parasite, insect and mammalian cells and more preferably in the cell types disclosed herein.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, helminth or other parasite, insect and mammalian cells, such as, but not limited to, tac, lac, trp, trc, oxy-pro, omp/lpp, rrnB, bacteriophage lambda (such as lambdap$_L$ and lambdap$_R$ and fusions that include such promoters), bacteriophage T7, T7lac, bacteriophage T3, bacteriophage SP6, bacteriophage SP01, metallothionein, alphamating factor, Pichia alcohol oxidase, alphavirus subgenomic promoters (such as Sindbis virus subgenomic promoters), antibiotic resistance gene, baculovirus, *Heliothis zea* insect virus, herpes virus, vaccinia virus, raccoon poxvirus, other poxvirus, adenovirus, cytomegalovirus (such as intermediate early promoters), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins).

Recombinant molecules of the present invention may also (a) contain secretory signals (i.e., signal segment nucleic acid sequences) to enable an expressed protein of the present invention to be secreted from the cell that produces the protein and/or (b) contain fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments. Suitable fusion segments encoded by fusion segment nucleic acids are disclosed herein. Eukaryotic recombinant molecules may include intervening and/or untranslated sequences surrounding and/or within the nucleic acid sequences of nucleic acid molecules of the present invention.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a cell include nucleic acid molecules disclosed herein (e.g. nucleic acids encoding BNRF1 (Epstein Barr virus: X67777 or gi:59165) and analogs thereof.))

Yet another embodiment of the present invention relates to a method to identify whether a first amino acid sequence includes a protein and/or peptide that is involved in purine biosynthesis and/or viral infection processes, and/or that interacts with telomerase, and/or that is involved in malignant transformation. This method includes the steps of (a) searching the first amino acid sequence to identify at least one amino acid sequence substantially similar to and having significant homology to either BNRF1 and/or FGARAT (Note: human AB002359 or gi:2224662; FGARAT *Drosophila melanogaster* is: U00683 or gi:414422) such that an alignment of such sequences identifies one first alignment wherein the probability thereof is not consistent with chance.

Still other embodiments of the present invention are directed to antibodies directed against proteins of the present invention (as referred to above). Also included in the present invention is the use of such proteins, nucleic acid molecules, antibodies and other inhibitors, as well as therapeutic compositions, to treat malignant conditions, viral infections, to affect purine synthesis and to alter the stability of a telomere within a cell.

It is to be noted that the term "a" or "an" entity refers to one or more of that entity; for example, a protein refers to one or more proteins, or to at least one protein. As such, the terms "a" (or "an"), "one or more" and "at least one" can be used interchangeably herein. It is also to be noted that the terms "comprising", "including", and "having" can be used interchangeably. An isolated protein of the present invention can, for example, be obtained from its natural source, be produced using recombinant DNA technology, or be synthesized chemically. As used herein, an isolated protein of the present invention can be a full-length protein or any homologue of such a protein, such as a protein in which amino acids have been deleted (e.g., a truncated version of the protein, such as a peptide), inserted, inverted, substituted and/or derivatized (e.g., by glycosylation, phosphorylation, acetylation, myristoylation, prenylation, palmitation, amidation and/or addition of glycosylphosphatidyl inositol). A homologue of a protein of the present invention is a protein having an amino acid sequence that is sufficiently similar to a natural protein amino acid sequence of the present invention that a nucleic acid sequence encoding the homologue is capable of hybridizing under stringent conditions to (i.e., with) a nucleic acid molecule encoding the natural protein of the present invention (i.e., to the complement of the nucleic acid strand encoding the natural protein amino acid sequence). A nucleic acid sequence complement of any nucleic acid sequence of the present invention refers to the nucleic acid sequence of the nucleic acid strand that is complementary to (i.e., can form a complete double helix with) the strand for which the sequence is cited. It is to be noted that a double-stranded nucleic acid molecule of the present invention for which a nucleic acid sequence has been determined for one strand that is represented by a SEQ ID NO also comprises a complementary strand having a sequence that is a complement of that SEQ ID NO. As such, nucleic acid molecules of the present invention, which can be either double-stranded or single-stranded, include those nucleic acid molecules that form stable hybrids under stringent hybridization conditions with either a given SEQ ID NO denoted herein and/or with the complement of that SEQ ID NO, which may or may not be denoted herein. Methods to deduce a complementary sequence are known to those skilled in the art.

As used herein, stringent hybridization conditions refer to standard hybridization conditions under which nucleic acid molecules, including oligonucleotides, are used to identify similar nucleic acid molecules. Such standard conditions are disclosed, for example, in Sambrook et al., *Molecular Cloning: A Laboratory Manual,* Cold Spring Harbor Labs Press, 1989; Sambrook et al., ibid., is incorporated by reference herein in its entirety. Stringent hybridization conditions typically permit isolation of nucleic acid molecules having at least about 70% nucleic acid sequence identity with the nucleic acid molecule being used to probe in the hybridization reaction. Formulae to calculate the appropriate hybridization and wash conditions to achieve hybridization permitting 30% or less mismatch of nucleotides are disclosed, for example, in Meinkoth et al., 1984, *Anal. Biochem.* 138, 267–284; Meinkoth et al., ibid., is incorporated by reference herein in its entirety.

The minimal size of a protein homologue of the present invention is a size sufficient to be encoded by a nucleic acid molecule capable of forming a stable hybrid with the complementary sequence of a nucleic acid molecule encoding the corresponding natural protein. As such, the size of the nucleic acid molecule encoding such a protein homologue is dependent on nucleic acid composition and percent homology between the nucleic acid molecule and complementary sequence as well as upon hybridization conditions per se (e.g., temperature, salt concentration, and formamide concentration). The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode a protein homologue of the present invention is from about 12 to about 18 nucleotides in length. There is no limit, other than a practical limit, on the maximal size of such a nucleic acid molecule in that the nucleic acid molecule can include a portion of a gene, an entire gene, or multiple genes, or portions thereof. Similarly, the minimal size of a protein homologue of the present invention is from about 4 to about 6 amino acids in length, with preferred sizes depending on whether a full-length, multivalent (i.e., fusion protein having more than one domain each of which has a function), or functional portions of such proteins are desired.

Protein homologues of the present invention can be the result of natural allelic variation or natural mutation. protein homologues of the present invention can also be produced using techniques known in the art including, but not limited to, direct modifications to the protein or modifications to the gene encoding the protein using, for example, classic or recombinant DNA techniques to effect random or targeted mutagenesis.

A homologue of a protein of the present invention also includes a homologue that, when the homologue is administered to an animal as an immunogen, using techniques known to those skilled in the art, the animal will produce an immune response against at least one epitope of a natural protein of the present invention. The ability of a protein to effect an immune response, can be measured using techniques known to those skilled in the art.

As used herein, a mimetope of a protein of the present invention refers to any compound that is able to mimic the activity of such a protein, often because the mimetope has a structure that mimics the protein. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic or inorganic molecules, and screening such samples by affinity chromatography techniques using the corresponding binding partner.

One embodiment of the present invention is a fusion protein that includes an protein-containing domain attached to one or more fusion segments. Suitable fusion segments for use with the present invention include, but are not limited to, segments that can: enhance a protein's stability; act as an immunopotentiator to enhance an immune response against a protein of the present invention; and/or assist purification of a protein (e.g., by affinity chromatography). A suitable fusion segment can be a domain of any size that has the desired function (e.g., imparts increased stability, imparts increased immunogenicity to a protein, and/or simplifies purification of a protein). Fusion segments can be joined to amino and/or carboxyl termini of the domain of the protein of the present invention and can be susceptible to cleavage in order to enable straight-forward recovery of a protein of the present invention. Fusion proteins are preferably produced by culturing a recombinant cell transformed with a fusion nucleic acid molecule that encodes a protein including the fusion segment attached to either the carboxyl and/or amino terminal end of a domain.

In another embodiment, a protein of the present invention also includes at least one additional protein segment that is capable of protecting an animal from one or more diseases. Such a multivalent protective protein can be produced by culturing a cell transformed with a nucleic acid molecule comprising two or more nucleic acid domains joined together in such a manner that the resulting nucleic acid molecule is expressed as a multivalent protective compound containing at least two protective compounds, or portions thereof, capable of protecting an animal from diseases caused, for example, by at least one infectious agent.

Examples of multivalent protective compounds include, but are not limited to, a protein of the present invention attached to one or more compounds protective against one or more other infectious agents, particularly an agent that infects humans, cats, dogs, cattle and/or horses, such as, but not limited to: viruses (e.g., adenoviruses, caliciviruses, coronaviruses, distemper viruses, hepatitis viruses, herpes viruses, immunodeficiency viruses, infectious peritonitis viruses, leukemia viruses, oncogenic viruses, panleukopenia viruses, papilloma viruses, parainflueriza viruses, parvoviruses, rabies viruses, and reoviruses, as well as other cancer-causing or cancer-related viruses); bacteria (e.g., Actinomyces, Bacillus, Bacteroides, Bordetella, Bartonella, Borrelia, Brucella, Campylobacter, Capnocytophaga, Clostridium, Corynebacterium, Coxiella, Dermatophilus, Enterococcus, Ehrlichia, Escherichia, Francisella, Fusobacterium, Haemobartonella, Helicobacter, Klebsiella, L-form bacteria, Leptospira, Listeria, Mycobacteria, Mycoplasma, Neorickettsia, Nocardia, Pasteurella, Peptococcus, Peptostreptococcus, Proteus, Pseudornonas, Rickettsia, Rochalirnaea, Salmonella, Shigella, Staphylococcus, Streptococcus, and Yersinia; fungi and fungal-related microorganisms (e.g., Absidia, Acremoniurn, Alternaria, Aspergillus, Basidiobolus, Bipolaris, Blastomyces, Candida, Chlarnydia, Coccidioides, Conidiobolus, Cryptococcus, Curvalaria, Epidermophyton, Exophiala, Geotrichum, Histoplasma, Madurella, Malassezia, Microsporum, Moniliella, Mortierella, Mucor, Paecilomryces, Penicillium, Phialemonium, Phialophora, Prototheca, Pseudallescheria, Pseudomicrodochium, Pythium, Rhinosporidium, Rhizopus, Scolecobasidium, Sporothrix, Stemphylium, Trichophyton, Trichosporon, and Xylohypha; and other parasites (e.g., Babesia, Balantidiurn, Besnoitia, Cryptosporidium, Eimeria, Encephalitozoon, Entamoeba, Giardia, Hammondia, Hepatozoon, Isospora, Leishmania, Microsporidia, Neospora, Nosema, Pentatrichomonas, Plasmodium, Pneumocystis, Sarcocystis, Schistosoma, Theileria, Toxoplasma, and Trypanosoma.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention and/or other proteins useful in the production of multivalent vaccines). Host cells of the present invention either can be endogenously (i.e., naturally) capable of producing proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite (including helminth, protozoa and ectoparasite), other insect, other animal and plant cells. Preferred host cells include bacterial, mycobacterial, yeast, helminth, insect and mammalian cells. More preferred host cells include Salmonella, Escherichia, Bacillus, Listeria, Saccharomyces, Spodoptera, Mycobacteria, Trichoplusia, BHK (baby hamster kidney) cells, MDCK cells (normal dog kidney cell line for canine herpesvirus cultivation), CRFK cells (normal cat kidney cell line for feline herpesvirus cultivation), CV-1 cells (African monkey kidney cell line used, for example, to culture raccoon poxvirus), COS (e.g., COS-7) cells, and Vero cells. Particularly preferred host cells are *Escherichia coli*, including *E. coli* K-12 derivatives; Salmonella typhi; *Salmonella typhimurium*, including attenuated strains such as UK-1 $_x$3987 and SR-11 $_x$4072; *Spodoptera frugiperda; Trichoplusia ni;* BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK$^{31}$ cells a nd/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a host cell. Nucleic acid molecules of the present invention can be operatively linked to expression vectors containing regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in plant, yeast, insect, mammalian or bacterial cells. A variety of such transcription control sequences are known to those skilled in the art.

A recombinant molecule of the present invention is a molecule that can include at least one of any nucleic acid molecule heretofore described operatively linked to at least one of any transcription control sequence capable of effectively regulating expression of the nucleic acid molecule(s) in the cell to be transformed, examples of which are disclosed herein.

A recombinant cell of the present invention includes any cell transformed with at least one of any nucleic acid molecule of the present invention. Suitable and preferred nucleic acid molecules as well as suitable and preferred recombinant molecules with which to transfer cells are disclosed herein.

Recombinant cells of the present invention can also be co-transformed with one or more recombinant molecules including nucleic acid molecules encoding one or more proteins of the present invention and one or more other proteins useful in the production of multivalent vaccines.

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Isolated proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective, medium refers to any medium in which a cell is cultured to produce a protein of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane.

The phrase "recovering the protein" refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and preferably should be capable of stimulating the production of antibodies in a treated animal.

The present invention also includes isolated (i.e., removed from their natural milieu) antibodies capable of selectively binding to an protein of the present invention or a mimetope thereof (e.g., antibodies). As used herein, the term "selectively binds to" refers to the ability of antibodies of the present invention to preferentially bind to specified proteins and mimetopes thereof of the present invention. Binding can be measured using a variety of methods standard in the art including enzyme immunoassays (e.g., ELISA), immunoblot assays, etc.; see, for example, Sambrook et al., ibid. An antibody preferably selectively binds to an protein in such a way as to reduce the activity of that protein.

Isolated antibodies of the present invention can include serum containing such antibodies, or antibodies that have been purified to varying degrees. Antibodies of the present invention can be polyclonal or monoclonal, functional equivalents such as antibody fragments and genetically-engineered antibodies, including single chain antibodies or chimeric antibodies that can bind to more than one epitope.

A preferred method to produce antibodies of the present invention includes (a) administering to an animal an effective amount of a protein, peptide or mimetope thereof of the present invention to produce the antibodies and (b) recovering the antibodies. In another method, antibodies of the present invention are produced recombinantly using techniques as heretofore disclosed to produce proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Targeting carriers are herein referred to as "delivery vehicles." Delivery vehicles of the present invention are capable of delivering a therapeutic composition of the present invention to a target site in an animal. A "target site" refers to a site in an animal to which one desires to deliver a therapeutic composition. For example, a target site can be a malignant tumor cell, a non-malignant tumor cell, a lymph node or a lesion caused by an infectious agent, or an area around such cell, tumor or lesion, which is targeted by direct injection or delivery using liposomes or other delivery vehicles. Examples of delivery vehicles include, but are not limited to, artificial and natural lipid-containing delivery vehicles. Natural lipid-containing delivery vehicles include cells and cellular membranes. Artificial lipid-containing delivery vehicles include liposomes and micelles. A delivery vehicle of the present invention can be modified to target to a particular site in an animal, thereby targeting and making use of a nucleic acid molecule of the present invention at that site. Suitable modifications include manipulating the chemical formula of the lipid portion of the delivery vehicle and/or introducing into the vehicle a compound capable of specifically targeting a delivery vehicle to a preferred site, for example, a preferred cell type. Specifically targeting refers to causing a delivery vehicle to bind to a particular cell by the interaction of the compound in the vehicle to a molecule on the surface of the cell. Suitable targeting compounds include ligands capable of selectively (i.e., specifically) binding another molecule at a particular site. Examples of such ligands include antibodies, antigens, receptors and receptor ligands. For example, an antibody specific for an antigen found on the surface of a cancer cell can be introduced to the outer surface of a liposome delivery vehicle so as to target the delivery vehicle to the cancer cell. Tumor cell ligands include ligands capable of binding to a molecule on the surface of a tumor cell. Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with particular cells having particular charge characteristics.

A preferred delivery vehicle of the present invention is a liposome. A liposome is capable of remaining stable in an animal for a sufficient amount of time to deliver a nucleic acid molecule of the present invention to a preferred site in the animal. A liposome of the present invention is preferably stable in the animal into which it has been administered for at least about 30 minutes, more preferably for at least about 1 hour and even more preferably for at least about 24 hours.

A liposome of the present invention comprises a lipid composition that is capable of targeting a nucleic acid molecule of the present invention to a particular, or selected, site in an animal. Preferably, the lipid composition of the liposome is capable of targeting to any organ of an animal, more preferably to the lung, liver, spleen, heart, brain, lymph nodes and skin of an animal.

A liposome of the present invention comprises a lipid composition that is capable of fusing with the plasma membrane of the targeted cell to deliver a nucleic acid molecule into a cell. Preferably, the transfection efficiency of a liposome of the present invention is at least about 0.5 microgram ($\mu$g) of DNA per 16 nanomole (nmol) of liposome delivered to about $10^6$ cells, more preferably at least about 1.0 $\mu$g of DNA per 16 nmol of liposome delivered to about $10^6$ cells, and even more preferably at least about 2.0 $\mu$g of DNA per 16 nmol of liposome delivered to about $10^6$ cells.

A preferred liposome of the present invention is between about 100 and about 500 nanometers (nm), more preferably between about 150 and about 450 nm and even more preferably between about 200 and about 400 nm in diameter.

Suitable liposomes for use with the present invention include any liposome. Preferred liposomes of the present invention include those liposomes standardly used in, for example, gene delivery methods known to those of skill in the art. More preferred liposomes comprise liposomes having a polycationic lipid composition and/or liposomes having a cholesterol backbone conjugated to polyethylene glycol. Even more preferred liposomes include liposomes produced according to the method described in Example 2.

In one embodiment, a liposome of the present invention comprises a compound capable of targeting the liposome to a tumor cell. Such a liposome preferably includes a tumor cell ligand exposed on the outer surface of the liposome.

Complexing a liposome with a nucleic acid molecule of the present invention can be achieved using methods standard in the art. A suitable concentration of a nucleic acid molecule of the present invention to add to a liposome includes a concentration effective for delivering a sufficient amount of nucleic acid molecule to a cell such that the cell can produce sufficient superantigen and/or cytokine protein to regulate effector cell immunity in a desired manner. Preferably, nucleic acid molecules are combined with liposomes at a ratio of from about 0.1 $\mu$g to about 10 $\mu$g of nucleic acid molecule of the present invention per about 8 nmol liposomes, more preferably from about 0.5 $\mu$g to about 5 $\mu$g of nucleic acid molecule per about 8 nmol liposomes, and even more preferably about 1.0 $\mu$g of nucleic acid molecule per about 8 nmol liposomes.

Another preferred delivery vehicle comprises a recombinant virus particle vaccine. A recombinant virus particle vaccine of the present invention includes a therapeutic composition of the present invention, in which the recombinant molecules contained in the composition are packaged in a viral coat that allows entrance of DNA into a cell so that the DNA is expressed in the cell. A number of recombinant virus particles can be used, including, but not limited to, those based on alphaviruses, poxviruses, adenoviruses, herpes viruses, arena virus and retroviruses.

Another preferred delivery vehicle comprises a recombinant cell vaccine. Preferred recombinant cell vaccines of the present invention include tumor vaccines, in which allogeneic (i.e., cells derived from a source other than a patient, but that are histiotype compatible with the patient) or autologous (i.e., cells isolated from a patient) tumor cells are transfected with recombinant molecules contained in a therapeutic composition, irradiated and administered to a patient by, for example, intradermal, intravenous or subcutaneous injection. Therapeutic compositions to be administered by tumor cell vaccine, include recombinant molecules of the present invention without carrier. Tumor cell vaccine treatment is useful for the treatment of both tumor and metastatic cancer. Use of a tumor vaccine of the present invention is particular useful for treating metastatic cancer, including preventing metastatic disease, as well as, curing existing metastatic disease. Methods for developing and administering include those standard in the art (see for example, Dranoff et al., Proc. Natl. Acad. Sci. USA 90:3539–3543, 1993, which is incorporated herein by reference in its entirety).

A therapeutic composition of the present invention is useful for the treatment of a variety of diseases, including, but not limited to, cancer, autoimmune disease, infectious diseases, and other diseases that can be alleviated by either stimulating or suppressing T cell activity. As used herein, the term "treatment" refers to protecting an animal from a disease or alleviating a disease in an animal. A therapeutic composition of the present invention is advantageous for the treatment of cancer in that the composition overcomes the mechanisms by which cancer cells avoid immune elimination (i.e., by which cancer cells avoid the immune response effected by the animal in response to the disease). Cancer cells can avoid immune elimination by, for example, being only slightly immunogenic, modulating cell surface antigens and inducing immune suppression.

A therapeutic composition of the present invention is useful for the treatment of cancers, both tumors and metastatic forms of cancer. Treatment with the therapeutic composition overcomes the disadvantages of traditional treatments for metastatic cancers. For example, compositions of the present invention can target dispersed metastatic cancer cells that cannot be treated using surgical methods. In addition, administration of such compositions do not result in the harmful side effects caused by chemotherapy and radiation therapy.

A therapeutic composition of the present invention is preferably used to treat cancers, including, but not limited to, melanomas, squamous cell carcinoma, breast cancers, head and neck carcinomas, thyroid carcinomas, soft tissue sarcomas, bone sarcomas, testicular cancers, prostatic cancers, ovarian cancers, bladder cancers, skin cancers, brain cancers, angiosarcomas, hemangiosarcomas, mast cell tumors, primary hepatic cancers, lung cancers, pancreatic cancers, gastrointestinal cancers, renal cell carcinomas, hematopoietic neoplasias, leukemias and lymphomas. Particularly preferred cancers to treat with a therapeutic composition of the present invention, include melanomas, lung cancers, thyroid carcinomas, breast cancers, renal cell carcinomas, squamous cell carcinomas, brain tumors and skin cancers. A therapeutic composition of the present invention is useful for treating tumors that can form in such cancers, including malignant and benign tumors.

In order to treat an animal with disease, a therapeutic composition of the present invention is administered to the animal in an effective manner such that the composition is capable of treating that animal from disease. For example, a recombinant molecule, when administered to an animal in an effective manner, is able to stimulate effector cell immunity in a manner that is sufficient to alleviate the disease afflicting the animal. According to the present invention, treatment of a disease refers to alleviating a disease and/or preventing the development of a secondary disease resulting from the occurrence of a primary disease.

An effective administration protocol (i.e., administering a therapeutic composition in an effective manner) comprises suitable dose parameters and modes of administration that result in treatment of a disease. Effective dose parameters and modes of administration can be determined using methods standard in the art for a particular disease. Such methods include, for example, determination of survival rates, side effects (i.e., toxicity) and progression or regression of disease. In particular, the effectiveness of dose parameters and modes of administration of a therapeutic composition of the present invention when treating cancer can be determined by assessing response rates. Such response rates refer to the percentage of treated patients in a population of patients that respond with either partial or complete remission. Remission can be determined by, for example, measuring tumor size or microscopic examination for the presence of cancer cells in a tissue sample.

In accordance with the present invention, a suitable single dose size is a dose that is capable of treating an animal with disease when administered one or more times over a suitable time period. Doses can vary depending upon the disease being treated. In the treatment of cancer, a suitable single dose can be dependent upon whether the cancer being treated is a primary tumor or a metastatic form of cancer. Doses of a therapeutic composition of the present invention suitable for use with direct injection techniques can be used by one of skill in the art to determine appropriate single dose sizes for systemic administration based on the size of an animal.

The number of doses administered to an animal is dependent upon the extent of the disease and the response of an individual patient to the treatment. For example, a large tumor may require more doses than a smaller tumor. In some cases, however, a patient having a large tumor may require fewer doses than a patient with a smaller tumor, if the patient with the large tumor responds more favorably to the therapeutic composition than the patient with the smaller tumor. Thus, it is within the scope of the present invention that a suitable number of doses includes any number required to cause regression of a disease. A preferred protocol is monthly administrations of single doses (as described above) for up to about 1 year. A preferred number of doses of a therapeutic composition comprising a superantigen-encoding recombinant molecule; or a combination of a superantigenencoding recombinant molecule, with a cytokine-encoding recombinant molecule and/or a chemokine-encoding recombinant molecule in a non-targeting carrier or complexed with liposomes in order to treat a tumor is from about 1 to about 10 administrations per patient, preferably from about 2 to about 8 administrations per patient, and even more preferably from about 3 to about 5 administrations per patient. Preferably, such administrations are given once every 2 weeks until signs of remission appear, then once a month until the disease is gone.

A therapeutic composition is administered to an animal in a fashion to enable expression of an introduced recombinant molecule of the present invention into a curative protein in the animal to be treated for disease. A therapeutic composition can be administered to an animal in a variety of methods including, but not limited to, local administration of the composition into a site in an animal. Examples of such sites include lymph nodes, a site that contains abnormal cells or pathogens to be destroyed (e.g., injection locally within the area of a tumor or a lesion); and systemic administration.

Therapeutic compositions to be delivered by local administration include: (a) recombinant molecules of the present invention in a non-targeting carrier (e.g., as "naked" DNA molecules, such as is taught, for example in Wolff et al., 1990, *Science* 247, 1465–1468); and (b) recombinant molecules of the present invention complexed to a delivery vehicle of the present invention. Suitable delivery vehicles for local administration comprise liposomes. Delivery vehicles for local administration can further comprise ligands for targeting the vehicle to a particular site (as described in detail herein).

A preferred method of local administration is by direct injection. Direct injection techniques are particularly useful for the treatment of disease by, for example, injecting the composition into a mass formed by abnormal cells, a lymph node or a granuloma mass induced by pathogens. Preferably, a recombinant molecule of the present invention complexed with a delivery vehicle is administered by direct injection into or locally within the area of a tumor mass, a lymph node, a granuloma mass or a cancer cell. Administration of a composition locally within an area of a mass or a cell refers to injecting the composition centimeters and preferably, millimeters within the mass or the cell. A preferred tumor mass to inject includes discrete inner body and cutaneous solid tumors. A preferred inner body tumor to inject includes a discrete solid tumor that forms in the brain, breast, liver, kidney, colon, prostate, testicular, ovary, spleen and/or lymph node. A preferred cutaneous tumor to inject includes a discrete solid melanoma.

A preferred lymph node to inject includes a draining lymph node that "drains" a site containing abnormal cells or pathogens. As used herein, the term "draining lymph node" refers to a lymph node that is located downstream of a site containing abnormal cells or pathogens is based on the direction of the lymphatic flow of an animal (see general discussion in Hole, *Human Anatomy and Physiology*, Edward G. Jaffe, ed., Wm. C Brown Publishers, Dubuque, Iowa; and G.C. Christiansen et al., *Anatomy of the Dog*, W. B. Saunders Publishers, Philadelphia, Pa., 1979; both of which are incorporated herein by this reference). A preferred draining lymph node to inject comprises the draining lymph node most proximal to a site containing abnormal cells or pathogens. Thus, a skilled artisan can choose the site of lymph node injection based upon the location of the site containing abnormal cells or pathogens. Examples of lymph nodes to injection include: the mandibular lymph node if a tumor is located in the oral cavity; and the superficial cervical lymph node of a tumor is located in the front leg region. Effector cells travel from a site containing abnormal cells or pathogens. Injection of a therapeutic composition of the present invention into a lymph node can result in expression of a superantigen, a cytokine and/or a chemokine by an effector cell from the lymph node or that has drained into the lymph node. Such expression can result in the activation of T lymphocytes, which can travel back to the site containing abnormal cells or pathogens to enhance the immune response at the site.

Another method of local administration is to contact a therapeutic composition of the present invention in or around a surgical wound. For example, a patient can undergo surgery to remove a tumor. Upon removal of the tumor, the therapeutic composition can be coated on the surface of tissue inside the wound or the composition can be injected into areas of tissue inside the wound. Such local administration is useful for treating cancer cells not excised by the surgical procedure, as well as, preventing recurrence of the primary tumor or development of a secondary tumor in the area of the surgery.

In one embodiment, a therapeutic composition of the present invention can be introduced to a tumor cell in vi vo. In another embodiment, a therapeutic composition of the present invention can be introduced to a non-tumor cell in vivo or i n vitro. Methods to introduce a therapeutic composition in vivo are disclosed herein. Methods to introduce a therapeutic composition in vitro include methods standard in the art, such as culturing cells in the presence of a therapeutic composition for a sufficient amount of time to enable a nucleic acid molecule of the present invention to pass through the plasma membrane in a cell and subsequently to be expressed in the cell.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site, preferably ligands for targeting the vehicle to a site of a cancer or a lesion (depending upon the disease being treated). For cancer treatment, ligands capable of selectively binding to a cancer cell or to a cell within the area of a cancer cell are preferred. Systemic administration is useful for the treatment of both tumor and metastatic cancer and systemic infectious diseases. Systemic administration is particularly useful for the treatment of metastatic forms of cancer, in which the cancer cells are dispersed (i.e., not localized within a single tumor mass). Systemic administration is particularly advantageous when organs, in particular difficult to reach organs (e.g., heart, spleen, lung or liver) are the targeted sites of treatment.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., *Proc. Natl. Acad. Sci. USA* 189:11277–11281, 1992, which is incorporated herein by reference in its entirety). Oral delivery can be performed by complexing a therapeutic composition of the present invention to a carrier capable of withstanding degradation by digestive enzymes in the gut of an animal. Examples of such carriers, include plastic capsules or tablets, such as those known in the art. Topical delivery can be performed by mixing a therapeutic composition of the present invention with a lipophilic reagent (e.g., DMSO) that is capable of passing into the skin.

Therapeutic compositions of the present invention can be administered to any animal, preferably to mammals and birds, and more preferably to humans, house pets, economic produce animals and zoo animals. Economic produce animals include animals to be consumed or that produce useful products (e.g., sheep for wool production). Zoo animals include those animals harbored in zoos. Preferred animals to protect include humans, dogs, cats, sheep, cattle, horses and pigs, with humans and dogs being particularly preferred. While a therapeutic composition of the present invention is effective to treat disease in inbred species of animals, the composition is particularly useful for treating outbred species of animals, in particular those having tumors.

In one embodiment, an immunogen comprises a nucleic acid molecule encoding an immunogenic protein. Such immunogenencoding nucleic acid molecules can be designed by those of skill in the art based upon the amino acid sequence of the immunogen. In addition, a recombinant molecule encoding an immunogen of the present invention can be produced using the recombinant DNA technology disclosed herein and known to those of skill in the art. In other embodiments, an immunogen can comprise a peptide, a polypeptide or a chemical compound as disclosed herein. All such embodiments of an immunogen are useful with an adjuvant of the present invention.

In order to treat an animal (i.e., vaccinate or remedy), an adjuvant composition of the present invention is administered to the animal in an effective manner such that the composition is capable of protecting an animal from or alleviating a disease. For example, an adjuvant, when administered to an animal in an effective manner, is able to stimulate effector cell immunity in a manner that is sufficient to prevent an initial or continued disease response by the subject animal.

An effective administration protocol (i.e., administering an adjuvant composition in an effective manner) comprises suitable dose parameters, and modes and times of administration that result in the treatment of an animal. Effective dose parameters and modes of administration can be determined using methods standard in the art for a particular adjuvant composition. Such methods include, for example: determination of side effects (i.e., toxicity) of an adjuvant composition; progression of a disease upon administration of an adjuvant composition; magnitude and/or duration of antibody response by an animal against an immunogen contained in an adjuvant composition; magnitude and/or duration of a cell mediated immune response in an animal against an adjuvant composition; similarity of an immune response to an adjuvant composition in different species of animals; and/or effect of breed (in non-human animals) or race (in humans) on responsiveness to an adjuvant composition. In particular, the effectiveness of dose parameters and modes of administration of an adjuvant composition of the present invention can be determined by assessing antibody production in vivo.

Also included in the present invention is a method to transfer a nucleic acid molecule into a given cell type that includes the step of administering to a population of cells including that cell type a composition comprising a delivery vehicle transformed with the nucleic acid molecule encoding at least a portion of a protein of the present invention, wherein the vehicle is capable of fusing with that cell type and of transferring the nucleic acid molecule into that cell type. The method can be accomplished in vivo, ex vivo, or in vitro and can, in one embodiment, effect gene therapy. That is, the nucleic acid molecule is capable of correcting a genetic defect. A composition that is able to effect gene therapy includes a delivery vehicle that is genetically engineered to effect stable gene therapy in the targeted cell type by, for example, being able to effect integration of the gene into the host genome, maintaining the fused cell as a heterokaryon, or using other mechanisms to stabally maintain the gene in the treated cell type. Such a composition is administered to an organism in vivo, or ex vivo using techniques such as those developed for other gene delivery vehicles. For example, control of the expression of a BNRF1 -like nucleic acid sequence can ameliorate various diseases, including malignant or uncontrolled cell growth, as well as prolonging an organisms life through the ability to stablize telomere structures.

EXAMPLES

Example I

To establish FGARAT activity of BNRF1, genomic and CDNA clones encoding BNRF1 (available from Dr. Jim Jones at the National Jewish Medical and Research Center) are transfected into AdeB CHO cells. The transfection constructs will contain an antibiotic resistance gene, either neomycin or hygromycin resistance, and are selected for antibiotic resistance. Clones are isolated and then assayed for growth in purine-free medium. This protocol avoids the complexities of possible reversion of the CHO mutant alleles. After growth in a purine-free medium is achieved, the cells assayed are directly for FGARAT activity. BNRF1 protein in the transfectants is detected using an anti-FGARAT antibody or an anti-BNRF1 antibody. Antibodies that do not recognize CHO FGARAT are detected by examining wild-type and AdeB mutant CHO cells. One determines whether BNRF1 can correct the defects in the AdeA PRAT (NM 002703 or gi:4505978) deficient mutants and the AdePAB complex mutant using the same methods.

Example II

To test whether BNRF1 interacts with FGARAT, PRAT, and/or telomerase, a yeast interaction trap system is used. Briefly, in this system, protein-protein interactions are detected by requiring the protein-protein interaction for expression of a reporter gene in yeast cells. The reporter gene can be beta galactosidase, with expression of the reporter resulting in blue yeast colonies, or a leucine biosynthetic gene, which allows the leu⁻ yeast to grow in the absence of leucine. This system has been used successfully to detect novel interactions with mutant forms of cytosolic superoxide dismutase (SOD1). The yeast interaction trap system requires the construction of two expression constructs, one called the bait and one called the prey, e.g., expression constructs for FGARAT, PRAT and BNRF1. The proteins in the bait and prey vectors are co-expressed in reporter yeast strains using methods we have published previously.

BNRF1 either shows FGARAT activity, or it may simply interact with FGARAT or PRAT to modulate their activity.

Example III

The following example shows that the reported interaction of FGARAT with telomerase occurs in intact cells and that BNRF1 interacts with telomerase.

FGARAT interaction with telomerase is able to regulate purine synthesis by telomerase. Telomerase interacts with one of FGARAT, or PRAT and regulates both activities. Yeast interaction trap experiments are conducted with telomerase, FGARAT, PRAT, and BNRFL using telomerase clones. Since telomerase has at least two components and one associated protein, several clones are required. However, transfection with the telomerase reverse transcriptase alone is sufficient to immortalize normal human fibroblasts, so one may need only eamine this component of telomerase in the trap system (8). Necessary clones can be produced by PCR since the sequences of all the genes are known.

The above examples show the link between three of the major themes of modern cancer research and therapy, namely: 1) the role of viruses in human cancer; 2) the role of telomerase and telomere structure in cancer; and 3) the use of purine nucleotide analogues and inhibitors for the treatment of cancer and viral infections, including AIDS. These three lines of research have never been integrated in the way proposed here. FGARAT interaction with telomerase has regulatory significance since purine nucleotide synthesis can be modulated for telomerase activity as well as for immortalization induced by telomerase. Interference with this interaction offers a therapeutic target. In view of the showing that BNRF1 has FGARAT activity, the present inventors disclose a mechanism by which EBV assumes control over cellular purine nucleotide synthesis during viral infection, leading to new therapeutic approaches. For example, the FGARAT activity of BNRF1 is believed to make it susceptible to inhibition by molecules that specifically inhibit BNRF1 or other virally encoded molecules having FGARAT-like activity, as compared to (e.g., distinguished from) cellular FGARAT activity. The interaction between BNRF1 -like proteins and telomerase represents an aspect of the EBV induced immortalization process that is associated with increased telomerase activity and increased telomere stability. This interaction presents an additional target for cancer chemotherapy and viral infection. The present invention thus presents therapeutic interventions for viral infection, as well as for cancer, and illuminates steps of viral infection and cellular immortalization that are important for cancer.

What is claimed is:

1. A method for altering the activity of telomerase in a cell having a telomere and telomerase therein by administering to said cell, in vitro, an effective amount of a compound comprising a protein selected from the group consisting of BNRF1, FGARAT and PRAT .

2. A method to identify a compound that regulates the activity of telomerase in a cell, comprising: contacting a cell in vitro with a putative regulatory compound, said cell including a telomere and telomerase; assessing the ability of said putative regulatory compound to regulate the activity of telomerase, said putative regulatory compound having the ability to interfere with the interaction between telomerase and a protein encoded by a nucleic acid sequence encoding a protein selected from the group of BNRF1, FGARAT and PRAT.

* * * * *